United States Patent
Hashizume et al.

(10) Patent No.: US 9,982,139 B2
(45) Date of Patent: *May 29, 2018

(54) COLOR METALLIC PIGMENT, METHOD FOR PRODUCING SAME, AND COATING COMPOSITION AND COSMETIC CONTAINING SAME

(75) Inventors: Yoshiki Hashizume, Osaka (JP); Taro Morimitsu, Osaka (JP); Takayuki Nakao, Osaka (JP)

(73) Assignee: TOYO ALUMINIUM KABUSHIKI KAISHA, Osaka-Shi, Osaka (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/812,462

(22) PCT Filed: Jun. 8, 2011

(86) PCT No.: PCT/JP2011/063148
§ 371 (c)(1),
(2), (4) Date: Jan. 25, 2013

(87) PCT Pub. No.: WO2012/014573
PCT Pub. Date: Feb. 2, 2012

(65) Prior Publication Data
US 2013/0131187 A1 May 23, 2013

(30) Foreign Application Priority Data
Jul. 28, 2010 (JP) ................. 2010-169470

(51) Int. Cl.
C09C 3/06 (2006.01)
C09C 1/00 (2006.01)
C09C 1/62 (2006.01)
C09D 5/36 (2006.01)
A61K 8/28 (2006.01)
A61K 8/29 (2006.01)
A61Q 1/02 (2006.01)
A61K 8/02 (2006.01)
A61K 8/19 (2006.01)
C23C 18/54 (2006.01)
A61K 8/27 (2006.01)
C09C 1/64 (2006.01)
A61Q 1/06 (2006.01)
A61Q 1/08 (2006.01)
A61Q 3/02 (2006.01)
A61Q 5/06 (2006.01)

(52) U.S. Cl.
CPC ............ *C09C 3/063* (2013.01); *A61K 8/0258* (2013.01); *A61K 8/19* (2013.01); *A61K 8/27* (2013.01); *A61K 8/28* (2013.01); *A61K 8/29* (2013.01); *A61Q 1/02* (2013.01); *C09C 1/006* (2013.01); *C09C 1/0051* (2013.01); *C09C 1/62* (2013.01); *C09C 1/642* (2013.01); *C09D 5/36* (2013.01); *C23C 18/54* (2013.01); *A61K 2800/412* (2013.01); *A61K 2800/43* (2013.01); *A61K 2800/61* (2013.01); *A61K 2800/651* (2013.01); *A61Q 1/06* (2013.01); *A61Q 1/08* (2013.01); *A61Q 3/02* (2013.01); *A61Q 5/06* (2013.01); *C01P 2004/61* (2013.01); *C01P 2006/60* (2013.01); *C01P 2006/62* (2013.01); *C01P 2006/63* (2013.01); *C01P 2006/64* (2013.01); *C09C 2200/1054* (2013.01); *C09C 2200/1058* (2013.01); *C09C 2200/302* (2013.01); *C09C 2200/303* (2013.01); *C09C 2200/406* (2013.01); *C09C 2200/502* (2013.01)

(58) Field of Classification Search
None
See application file for complete search history.

(56) References Cited

U.S. PATENT DOCUMENTS

| | | | |
|---|---|---|---|
| 4,328,042 A | 5/1982 | Ostertag et al. | |
| 4,978,394 A | 12/1990 | Ostertag et al. | |
| 5,091,010 A | 2/1992 | Souma et al. | |
| 5,364,467 A | 11/1994 | Schmid et al. | |
| 5,607,504 A | 3/1997 | Schmid et al. | |
| 5,624,486 A * | 4/1997 | Schmid ............... | A61Q 1/02 106/31.65 |
| 5,763,086 A * | 6/1998 | Schmid ............... | A61Q 1/02 427/213 |
| 6,689,205 B1 * | 2/2004 | Bruckner et al. ..... | A61K 8/25 106/415 |
| 2003/0005859 A1 | 1/2003 | Andes et al. | |
| 2003/0017316 A1 | 1/2003 | Pfaff et al. | |
| 2003/0051634 A1 | 3/2003 | Takahashi | |
| 2003/0209169 A1 | 11/2003 | Andes et al. | |
| 2004/0194663 A1 | 10/2004 | Li et al. | |
| 2004/0244649 A1* | 12/2004 | Kato ................ | C09C 1/0078 106/403 |
| 2006/0150864 A1 | 7/2006 | Hashizume et al. | |
| 2008/0314284 A1 | 12/2008 | Li et al. | |
| 2008/0318012 A1* | 12/2008 | Domnick ............ | C09C 1/0015 428/216 |
| 2009/0017082 A1 | 1/2009 | Morimitsu et al. | |

FOREIGN PATENT DOCUMENTS

CN 1312840 A 9/2001
CN 1538995 A 10/2004
(Continued)

*Primary Examiner* — Bethany P Barham
*Assistant Examiner* — Ping Cao
(74) *Attorney, Agent, or Firm* — Birch, Stewart, Kolasch & Birch, LLP

(57) ABSTRACT

A color metallic pigment according to the present invention contains at least a metallic pigment, an amorphous silicon oxide film layer that is formed on the surface of the metallic pigment, a metal oxide layer that is formed on the surface of the amorphous silicon oxide film layer and contains a metal oxide other than silicon oxide, and metal particles that are formed on the surface of the metal oxide layer, wherein the metal particles are so formed as to directly cover a part of the metal oxide layer.

15 Claims, No Drawings

(56) References Cited

FOREIGN PATENT DOCUMENTS

| | | |
|---|---:|---|
| CN | 1694929 A | 11/2005 |
| EP | 1 270 683 A2 | 1/2003 |
| JP | 56-120771 A | 9/1981 |
| JP | 1-110568 A | 4/1989 |
| JP | 1-311176 A | 12/1989 |
| JP | 2-669 A | 1/1990 |
| JP | 6-32994 A | 2/1994 |
| JP | 7-258579 A | 10/1995 |
| JP | 8-209024 A | 8/1996 |
| JP | 2003-41150 A | 2/2003 |
| JP | 2003-49093 A | 2/2003 |
| JP | 2003-89758 A | 3/2003 |
| JP | 2003-131029 A | 5/2003 |
| JP | 2006-199920 A | 8/2006 |
| KR | 10-2008-0109758 A | 12/2008 |
| WO | WO 2007/094253 A1 | 8/2007 |

\* cited by examiner

COLOR METALLIC PIGMENT, METHOD FOR PRODUCING SAME, AND COATING COMPOSITION AND COSMETIC CONTAINING SAME

TECHNICAL FIELD

The present invention relates to a color metallic pigment having an excellent finish appearance, a method for producing the color metallic pigment, and a coating composition and a cosmetic each containing the color metallic pigment.

BACKGROUND ART

As for a color metallic pigment having an excellent design performance and a metallic feeling, a color metallic pigment produced by adhering a color pigment onto a metallic pigment is known heretofore. In the color metallic pigment, an organic pigment of a diketopyrrolopyrrole type, a quinacridon type, a dioxazine type, an isoindolinone type, a condensed azo type, a thren type, a perinone type, a perylene type, a phthalone type, a phthalocyanine type or the like, or an inorganic pigment such as iron oxide or carbon black is used as the color pigment to be adhered onto the metallic pigment.

However, the color metallic pigment as mentioned above has such a disadvantage that a color pigment adhered onto the surface of a metallic pigment is easily optically deteriorated by the reflection of light on the surface of the metallic pigment. For overcoming this disadvantage, it is necessary to select a pigment having relatively superior light resistance, such as phthalocyanine green, phthalocyanine blue and iron oxide, and therefore it is the today's situation that the design performance of the resultant color metallic pigment is restricted.

Meanwhile, with respect to a pearlescent pigment such as mica, a pigment produced by forming a covering film of silicon oxide, titanium oxide, a metal or the like on the surface of a pigment to impart an interference color to the pigment is known. However, the pearlescent pigment has such a disadvantage that the obliterating power is poor and, therefore the pearlescent pigment cannot obliterate an under layer satisfactorily when the pearlescent pigment is compounded to a coating material or an ink. For the purpose of avoiding this disadvantage, a metallic pigment that is colored by covering with an interference film made of silicon oxide, aluminum oxide, titanium oxide or the like has been disclosed as a metallic pigment having high obliterating power. This metallic pigment is, however, insufficient as a means for overcoming the disadvantage.

Japanese Patent Laying-Open No. 01-110568 (PTL 1) and Japanese Patent Laying-Open No. 02-000669 (PTL 2) disclose methods for allowing titanium oxide to be deposited on the surface of a metallic pigment by a sol-gel method. However, the methods have such disadvantages that it is impossible to obtain a metallic pigment having high chroma, and that the titanium oxide layer is converted into a highly active anatase phase and therefore the deterioration of a resin is accelerated when compounded to a coating material or the like, often leading to the deterioration in weather resistance.

Japanese Patent Laying-Open No. 56-120771 (PTL 3), Japanese Patent Laying-Open No. 01-311176 (PTL 4), and Japanese Patent Laying-Open No. 06-032994 (PTL 5) disclose methods for forming a composite layer made of a metal oxide such as iron oxide or titanium oxide and carbon, a metal, a metal oxide or the like on the surface of a metallic pigment by a gas phase method. However, when a gas phase method is employed, it is required to fluidize the metallic pigment, supply a precursor of the metal oxide, and allow the metal oxide to be deposited on the surface of the metallic pigment by heating. Further, this deposition method has such disadvantages that it is required to use a specialized apparatus, that there is a high risk of explosion of dusts of the metallic pigment, and that most of precursors of metal oxides are highly toxic and therefore are difficult to handle.

Japanese Patent Laying-Open No. 08-209024 (PTL 6) discloses a multi-layer covered metallic pigment basically having a dual layer structure including a colorless covering layer having a refractive index of less than or equal to 1.8 and a selectively absorbing layer having a refractive index of greater than or equal to 2.0. In PTL 6, a method is disclosed in which a metal oxide layer is formed on the surface of a metallic pigment by a CVD method (chemical vapor deposition method) or a method of hydrolyzing a metal compound in a solution. However, the CVD method, which is a gas phase method, has the above-mentioned disadvantage. Further, the method of hydrolyzing a metal compound in a solution to form a metal oxide layer has such a disadvantage that the hydrolysis reaction is carried out in a basic or acidic atmosphere containing a large amount of water and therefore a reaction between the metallic pigment and water occurs during the treatment step, leading to the aggregation of the metallic pigment or the runaway of the reaction.

Japanese Patent Laying-Open No. 07-258579 (PTL 7) discloses a luster pigment produced by coating a multi-layer film that includes a first layer containing silicon oxide, silicon oxide hydrate, aluminum oxide or aluminum oxide hydrate, a second layer containing a metal and/or a non-selectively absorbing metal oxide, and optionally a third layer containing a colorless or selectively absorbing metal oxide onto a backing layer made of an aluminum flake or the like.

However, in the method disclosed in PTL 7, the thickness of the first layer tends to be non-uniform and therefore good chroma cannot be achieved. Further, there is also a problem that the metal oxide tends to be released without being deposited on the surface of the backing layer during the formation of the first layer, reflected light is scattered by the released metal oxide particles, and therefore good metallic gloss cannot be achieved. Furthermore, as the method for forming the metal oxide layer on the first layer, a CVD method and an electroless plating method are disclosed. However, in the CVD method, there is a problem as mentioned above, and there is also a problem that it is difficult to deposit the metal oxide layer uniformly and particles on which the metal is not adhered may be often produced. When the electroless plating method is employed, there is also a problem that it is difficult to deposit the metal oxide layer finely and uniformly and the metal oxide layer is deposited non-uniformly in a scattered form, resulting in the development of undesirable chroma.

Japanese Patent Laying-Open No. 2003-049093 (PTL 8) discloses a multi-layer lucent pigment containing a metal base material and multiple layers each surrounding the base material completely, which is characterized by containing at least one layer pack that includes a colorless dielectric layer made of a material having a refractive index of less than or equal to 1.8 and a colorless dielectric layer made of a material having a refractive index of more than 1.8, and a selectively or non-selectively absorbing layer. Japanese Patent Laying-Open No. 2003-131029 (PTL 9) discloses an optical multi-layer system containing a metal base material and multiple layers applied onto both surfaces or one surface of the metal base material, which is characterized by having at least one layer pack that includes a colorless dielectric layer made of a material having a refractive index of less than or equal to 1.8 and a colorless dielectric layer made of a material having a refractive index of more than 1.8, and a selectively or non-selectively absorbing layer, wherein both of the layer pack and the selectively or non-selectively absorbing layer do not surround the metal oxide layer completely. Japanese Patent Laying-Open No. 2003-089758 (PTL 10) discloses a high-chroma scale-like pigment produced by covering the entire surface of a metal-oxide-covered scale-like base that is covered with a metal oxide to develop an interference color with a translucent metal thin film capable of enhancing the interference color. Japanese Patent Laying-Open No. 2003-041150 (PTL 11) discloses a highly corrosion-resistant scale-like metallic pigment characterized by having a covering layer, which contains a hydrated metal oxide made of a metal selected from the group consisting of silicon, aluminum, zirconium, titanium and tin, on the surface of a scale-like metal base that is treated with a phosphoric acid compound and/or a boric acid compound. However, in the methods disclosed in PTLs 8 to 11, there is a limitation on the degree of change in an interference color or the development of high chroma and, therefore, it is difficult to obtain a color metallic pigment having a satisfactory level of good design performance.

A color metallic pigment disclosed in International Patent Publication No. 2007/094253 pamphlet (PTL 12) has a structure containing a metallic pigment, an amorphous silicon oxide film layer formed on the surface of the metallic pigment, a metal layer formed on the surface of the amorphous silicon oxide film layer, and metal particles formed on the surface of the metal layer, and this constitution enables the achievement of good design performance. However, in the color metallic pigment, there is a problem that the adhesion state of the metal particles formed on the surface thereof is instable and, therefore, the color tone tends to be changed easily. There is also a problem that the metal layer that exists as an unavoidable component between the metal particles and the amorphous silicon oxide film layer is not registered as a cosmetic raw material and, therefore, the use of the metal layer for cosmetic purposes is restricted.

CITATION LIST

Patent Literature

PTL 1: Japanese Patent Laying-Open No. 01-110568
PTL 2: Japanese Patent Laying-Open No. 02-000669
PTL 3: Japanese Patent Laying-Open No. 56-120771
PTL 4: Japanese Patent Laying-Open No. 01-311176
PTL 5: Japanese Patent Laying-Open No. 06-032994
PTL 6: Japanese Patent Laying-Open No. 08-209024
PTL 7: Japanese Patent Laying-Open No. 07-258579
PTL 8: Japanese Patent Laying-Open No. 2003-049093
PTL 9: Japanese Patent Laying-Open No. 2003-131029
PTL 10: Japanese Patent Laying-Open No. 2003-089758
PTL 11: Japanese Patent Laying-Open No. 2003-041150
PTL 12: International Patent Publication No. 2007/094253 pamphlet

SUMMARY OF INVENTION

Technical Problem

The present invention has been made in the above-mentioned situations, and an object of the present invention is to provide: a color metallic pigment that can develop a wide variety of colors and a changeful interference color in a stable manner while keeping light resistance, weather resistance and obliterating power thereof at good levels; a method for producing the color metallic pigment; and a coating composition and a cosmetic each containing the color metallic pigment.

Solution to Problem

The color metallic pigment according to the present invention contains at least a metallic pigment, an amorphous silicon oxide film layer that is formed on the surface of the metallic pigment, a metal oxide layer that is formed on the surface of the amorphous silicon oxide film layer and contains a metal oxide other than silicon oxide, and metal particles that are formed on the surface of the metal oxide layer, wherein the metal particles are so formed as to directly cover a part of the metal oxide layer.

The metal oxide layer preferably contains an oxide of at least one element selected from the group consisting of Mg, Sn, Zn, Co, Ni, Fe, Zr, Ti, and Ce. Each of the metal particles preferably contains at least one element selected from the group consisting of Cu, Ni, and Ag.

The amorphous silicon oxide film layer preferably has a thickness ranging from 10 to 500 nm, and the metal particles preferably have an average particle diameter of less than or equal to 50 nm. With respect to the metallic pigment, an under layer may be formed thereon using a molybdenum compound, a phosphorus compound, aqueous hydrogen peroxide or the like prior to the formation of the amorphous silicon oxide film layer thereon. In the present invention, even when the under layer is formed on the surface of the metallic pigment, it is described as "the amorphous silicon oxide film layer is formed on the surface of the metallic pigment". Further, a weather-resistant covering film layer may be additionally formed on the metal particles. Examples of the weather-resistant covering film layer include a film containing only an oxide, a hydroxide or a hydrate each containing at least one element selected from the group consisting of aluminum, silicon and cerium, a film containing a mixture containing the oxide, the hydroxide or the hydrate, and a resin covering layer.

The present invention also relates to a method for producing the color metallic pigment, including at least the steps of: hydrolyzing an organosilicon compound in a solvent mainly containing a hydrophilic solvent and having a metallic pigment dispersed therein to allow amorphous silicon oxide to be deposited on the metallic pigment, thereby forming an amorphous silicon oxide film layer on the surface of the metallic pigment; allowing a metal oxide layer containing a metal oxide other than silicon oxide to be deposited on the surface of the amorphous silicon oxide film layer, thereby forming the metal oxide layer; and forming metal particles on the surface of the metal oxide layer by an electroless plating method.

In the production method, the metal oxide layer preferably contains an oxide of at least one element selected from the group consisting of Mg, Sn, Zn, Co, Ni, Fe, Zr, Ti, and Ce.

The present invention also relates to a coating composition and a cosmetic, each of which contains at least the above-mentioned color metallic pigment or a color metallic pigment produced by the above-mentioned method.

Advantageous Effects of Invention

According to the present invention, it becomes possible to obtain a color metallic pigment that can develop a wide variety of colors and a changeful interference color in a stable manner while keeping light resistance, weather resistance and obliterating power thereof at good levels, by a relatively simple and inexpensive means by forming at least an amorphous silicon oxide film layer, a metal oxide layer and metal particles on the surface of a metallic pigment. It becomes also possible to provide a coating composition that enables a coating film having an excellent finish appearance to be given and a cosmetic that contains the color metallic pigment, has excellent obliterating power and can develop a clear color, both using the above-mentioned color metallic pigment.

DESCRIPTION OF EMBODIMENTS

The present invention is described below in detail.

<Color Metallic Pigment>

The color metallic pigment according to the present invention contains at least a metallic pigment, an amorphous silicon oxide film layer that is formed on the surface of the metallic pigment, a metal oxide layer that is formed on the surface of the amorphous silicon oxide film layer and contains a metal oxide other than silicon oxide, and metal particles that are formed on the surface of the metal oxide layer, wherein only a part of the surface of the metal oxide layer is directly covered with the metal particles.

That is, in the color metallic pigment according to the present invention, the metal particles are not formed as a layer that entirely covers the metal oxide layer and the metallic pigment (i.e., base material). Therefore, there are a region that is covered with the metal particles and a region that is not covered with the metal particles. Thus, since the metal particles are so formed as to partially cover the metallic pigment (i.e., base material) as mentioned above, only a part of reflected light coming from the metallic pigment which passes through interspaces among the metal particles is recognized as visible light. As a result, reflective brightness from the metallic pigment is weakened and chroma (i.e., color) is developed. Further, in the color metallic pigment according to the present invention, an interference color having high chroma is developed as the result of the interference between reflected light coming from the surface of the metallic pigment (i.e., base material) and reflected light coming from the surfaces of the metal particles.

In the present invention, since the metal particles are so formed as to directly cover a part of the metal oxide layer, the detachment of the metal particles can be prevented due to good adhesion between the metal oxide layer and the metal particles and, therefore, a color metallic pigment having a wide variety of colors and a changeful interference color can be obtained in a stable manner.

The color metallic pigment according to the present invention is obtained by forming at least the amorphous silicon oxide film layer, the metal oxide layer and the metal particles on the surface of the metallic pigment. Therefore, the color metallic pigment is advantageous because the color metallic pigment can be produced by a relative simple means and can be imparted with a good finish appearance without sacrificing light resistance, weather resistance and obliterating power.

The color metallic pigment according to the present invention enables the formation of a coating composition that can provide a coating film having an excellent finish appearance when used in various coating materials and inks. The color metallic pigment can be particularly suitably used for a water-based coating material and ink. As mentioned above, the color metallic pigment according to the present invention can be extremely usefully used in industrial applications.

<Metallic Pigment>

Preferred examples of the metallic pigment to be used in the present invention include aluminum, copper, zinc, titanium, iron, nickel, chromium and alloys thereof, metal-covered flaky glasses and other metal-covered inorganic pigments. Among these pigments, aluminum is particularly preferably used from the viewpoint of design performance. The use of aluminum is advantageous, because a wide variety of color metallic pigments capable of developing an interference color can be obtained by forming the amorphous silicon oxide film layer thereon and superposing the metal particles on the amorphous silicon oxide film layer.

The preferred average particle diameter of the metallic pigment falls, for example, within the range from 2 to 300 μm. When the average particle diameter is greater than or equal to 2 μm, a color metallic pigment that can impart a good finish appearance and good obliterating power to the coating film can be obtained. When the average particle diameter is smaller than or equal to 300 μm, a color metallic pigment that can prevent the deterioration in the finish appearance of the coating film caused by insufficient dispersion of the color metallic pigment can be obtained. More preferably, the average particle diameter falls within the range from 5 to 100 μm. The term "average particle diameter of the metallic pigment" as used herein means an average longer diameter of the metallic pigment. The average particle diameter can be measured by a laser diffraction method.

The preferred thickness (average thickness) of the metallic pigment falls, for example, within the range from 0.01 to 5 μm. When the thickness is greater than or equal to 0.01 μm, a color metallic pigment that can retain the finish appearance thereof at a good level without deteriorating the light resistance and weather resistance of the coating film can be obtained. When the thickness is less than or equal to 5 μm, a color metallic pigment that can impart a good design performance and a wide variety of colors to the coating film can be obtained. More preferably, the thickness falls within the range from 0.02 to 1 μm. The thickness can be measured by a water surface diffusion area method (thickness=4000/S μm, wherein S represents a water surface diffusion area $(cm^2/g)$).

The preferred shape of the metallic pigment is a flaky (i.e., scale-like) shape, wherein the ratio of the average particle diameter A to the average thickness B (i.e., A/B) preferably falls within the range from 5 to 1000. When the A/B ratio is greater than or equal to 5, the coating film can have a good design performance and a wide variety of colors can be developed. When the A/B ratio is less than or equal to 1000, the metallic pigment is rarely deformed during the production of the color metallic pigment and the dispersibility of the color metallic pigment in the coating composition is rarely deteriorated, which is preferred. More preferably, the A/B ratio falls within the range from 15 to 500. The shape of the metallic pigment is particularly preferably a coin-like shape having a smooth surface and a round edge surface.

The metallic pigment to be used in the present invention can be obtained in the form of a powder that is produced by an atomizing method, a powder that is produced by grinding metal flakes by a wet ball milling method (i.e., hole method) or a dry ball milling method, or the like. The metallic pigment can also be obtained by depositing a metal thin film on a film or the like, then delaminating the metal thin film and grinding the metal thin film. A metal-covered flaky glass or other metal-covered pigment can be obtained by forming an element metal such as Ag, Cu, Ni, Fe, Co, Cr or Sn or an alloy of the metal in the form of a layer on a flaky or granular inorganic base material such as a flaky glass, mica, alumina, silica and titanium oxide by a technique such as electroless plating, deposition and sputtering.

<Amorphous Silicon Oxide Film Layer>

In the color metallic pigment according to the present invention, an amorphous silicon oxide film layer (layer formed from amorphous silicon oxide) is formed on the surface of the metallic pigment. The amorphous silicon oxide film layer is preferably formed on the entire surface of the metallic pigment. A case in which the surface of the metallic pigment contains a region on which the amorphous silicon oxide film layer is not formed does not depart from the scope of the present invention, as long as the effect of the present invention can be achieved. The amorphous silicon oxide film layer may be directly formed on the surface of the metallic pigment. However, it is preferred that another layer is interposed as an under layer between the metallic pigment and the amorphous silicon oxide film layer. An example of the under layer is, but is not limited to, a layer that includes a film containing only any one of an oxide, a hydroxide or a hydrate each containing at least one element selected from the group consisting of molybdenum, phosphorous and aluminum or a film containing a mixture containing the oxide, the hydroxide or the hydrate, as mentioned below. The under layer may contain one or more layers. When the under layer contains two or more layers, layers each having a different composition may be laminated on each other.

In the present invention, by forming the amorphous silicon oxide film layer, an effect of imparting a given refractive index and developing an interference color can be achieved. As for the method for forming the amorphous silicon oxide film layer, a method in which the metallic pigment and a solution containing an organosilicon compound are stirred or kneaded in the form of a slurry or a paste while keeping the atmosphere basic or acidic, or the like may be employed. In this manner, the amorphous silicon oxide film layer can be formed on the surface of the metallic pigment or on the surface of the metallic pigment having the under layer formed on the surface thereof.

Examples of the above-mentioned organosilicon compound include methyltriethoxysilane, methyltrimethoxysilane, tetraethoxysilane, tetramethoxysilane, tetraisopropoxysilane and condensation products thereof, γ-aminopropyltriethoxysilane, N-2-aminoethyl-3-aminopropyltriethoxysilane and N-2-aminoethyl-3-aminopropylmethyldimethoxysilane.

As for the solvent in which the silicon compound is to be dissolved to prepare a solution containing the organosilicon compound, a hydrophilic solvent is preferably used, such as methyl alcohol, ethyl alcohol, isopropyl alcohol, n-propyl alcohol, t-butyl alcohol, n-butyl alcohol, isobutyl alcohol, ethyl cellosolve, butyl cellosolve, propylene glycol monobutyl ether, dipropylene glycol monomethyl ether, propylene glycol monopropyl ether and acetone. It is desirable to compound water to the solvent in a sufficient amount for hydrolyzing the alkoxysilane.

In this manner, the amorphous silicon oxide film layer can be formed on the surface of the metallic pigment by hydrolyzing the organosilicon compound in a solvent mainly containing a hydrophilic solvent having the metallic pigment dispersed therein to allow amorphous silicon oxide to be deposited on the metallic pigment.

The amorphous silicon oxide film layer preferably has a thickness ranging from 10 to 500 nm, more preferably ranging from 10 to 100 nm. When the thickness is greater than or equal to 10 nm, the absorption state of the metal particles onto the surface of the metallic pigment surface becomes good and a coating film having higher chroma can be formed. When the thickness is less than or equal to 500 nm, the obliterating power of the coating film becomes excellent and the risk of excessively deteriorating the metallic appearance of the metallic pigment is reduced. The thickness of the amorphous silicon oxide film layer can be measured by the observation of a cross section using a transmission electron microscope (TEM).

As mentioned above, it is preferred to set the thickness of the amorphous silicon oxide film layer of the present invention to a value ranging from 10 to 500 nm, because the average particle diameters of the below-mentioned metal particles can be less than or equal to 50 nm and an effect of developing an interference color having particularly high chroma can be achieved.

The term "amorphous" as used herein with respect to the amorphous silicon oxide film layer means that no clear diffraction peak derived from silicon oxide is detected in the analysis of the crystal structure of the amorphous silicon oxide film layer by an X-ray diffraction method.

<Metal Oxide Layer>

In the present invention, a metal oxide layer containing a metal oxide other than silicon oxide is formed on the surface of the amorphous silicon oxide film layer. The metal oxide layer is preferably formed on the entire surface of the amorphous silicon oxide film layer. The surface of the amorphous silicon oxide film layer may have a region on which the metal oxide layer is not formed as a part thereof, and this embodiment does not depart from the scope of the present invention as long as the embodiment can achieve the effect of the present invention. By forming the metal oxide layer, the adhesion state of the below-mentioned metal particles onto the metal oxide layer becomes good, the metal particles can be densely and uniformly deposited with a regular spacing, and an interference color having high chroma can be developed.

When a metal layer containing a metal alone is formed in place of the metal oxide layer of the present invention, the metal particles can also be adsorbed. However, the metal oxide layer has a dramatically improved adsorption property compared with that of the metal layer. This is probably because the metal oxide layer has improved adhesion to the amorphous silicon oxide film layer compared with the metal layer.

The metal oxide layer preferably contains an oxide of at least one element selected from the group consisting of Mg (magnesium), Sn (tin), Zn (zinc), Co (cobalt), Ni (nickel), Fe (iron), Zr (zirconium), Ti (titanium) and Ce (cerium), particularly preferably a metal oxide of any one of Sn, Zn, Ti and Ce.

The method for forming the metal oxide layer is not particularly limited. Preferred examples of the method to be employed include: a method of hydrolyzing an alkoxide of a metal that constitutes the metal oxide layer by a sol-gel method to allow the metal oxide layer to be deposited on the amorphous silicon oxide film layer; a method of adding an alkali to a metal salt solution of a metal that constitutes the metal oxide layer to allow the metal oxide to be deposited by neutralization; and a method of bringing the metallic pigment having the amorphous silicon oxide film layer formed thereon into contact with a solution in which the organic metal compound has been dissolved in an organic solvent and then subjecting the resultant product to a heat treatment to oxidize the organic metal compound, thereby forming the metal oxide layer on the amorphous silicon oxide film layer.

Examples of the metal alkoxide to be used in the method of depositing the metal oxide layer by hydrolysis include tetraethoxytin and tetrabutoxytitanium, and a colloid solution having the metal alkoxide dispersed therein can be preferably used. Examples of the catalyst for the hydrolysis of the metal alkoxide include aqueous ammonia, ethylene diamine, monoethanolamine, diethanolamine, hydrazine and urea.

Examples of the metal salt to be used in the method of depositing the metal oxide layer by neutralization include tin chloride, tin fluoride, zinc chloride, titanyl sulfide, cerium nitrate and cerium acetate. Examples of a neutralizing agent for the metal salt include aqueous ammonia, sodium hydroxide, monoethanolamine and diethanolamine. Examples of the reaction solvent include water, ethanol, isopropyl alcohol, methyl propylene glycol and butyl cellosolve.

Examples of the organic metal compound to be used in the method using the organic metal compound include fatty acid metal salts such as cobalt naphthenate, nickel stearate, zirconium stearate and dibutyltin dilaurate. As for the solvent for dissolving the organic metal compound therein, any organic solvent in which the organic metal compound can be dissolved can be used, such as toluene, xylene, dimethylformamide, acetone, ethyl acetate, isopropyl alcohol, propylene glycol monomethyl ether and butyl cellosolve. The heat treatment temperature at which the organic metal compound is to be decomposed and oxidized is preferably 200 to 500° C. If the heat treatment temperature is lower than or equal to 200° C., it is difficult to oxidize the organic metal compound. If the heat treatment temperature is higher than or equal to 500° C., the aggregation of the metallic pigment may occur readily and the risk of ignition increases.

When the metal particles of the present invention are formed by electroless plating using a water-soluble metal salt, a layer containing Sn, Pt, Au, Pd, Zn or the like, which is generally used as a pretreatment for the electroless plating, may be formed on the metal oxide layer. Even when the layer is formed, it is described in the present invention as "the metal particles are so formed as to directly cover the metal oxide layer".

In the present invention, when the metal oxide layer is provided between the amorphous silicon oxide film layer and the pretreatment layer for the electroless plating, the adhesion force of the metal particles is stronger than that achieved by a conventional method (method described in PTL 12) and the color stability against mechanical, thermal or chemical attacks is excellent. In this case, it is also possible to achieve the development of a different color from those in the conventional method by forming the metal oxide layer on the amorphous silicon oxide film layer.

In the present invention, the thickness of the metal oxide layer is preferably less than or equal to 30 nm. In this case, the resultant color metallic pigment can be imparted with good chroma and a good interference color. The thickness of the metal oxide layer is more preferably set to a value falling within the range from 0.1 to 10 nm. The metal oxide layer may be uniformly or non-uniformly deposited on the surface of the amorphous silicon oxide film layer. If the metal oxide layer is too thick, the thickness of the resultant color metallic pigment is also increased and the obliterating power of the resultant color metallic pigment is deteriorated. If the metal oxide layer is too thin, the effect cannot be satisfactorily achieved and the development of the color is unstable. The thickness of the metal oxide layer can be measured by the observation of a cross section using a transmission electron microscope (TEM).

<Metal Particles>

In the color metallic pigment according to the present invention, the metal particles are formed on the surface of the metal oxide layer. The metal particles are characterized by being so formed as to directly cover a part of the surface of the metal oxide layer.

The color metallic pigment according to the present invention has a region on which the metal particles are not formed, i.e., a region which is not covered with the metal particles. By employing this constitution, interference occurs between reflected light coming from the surfaces of the metal particles and reflected light passing through the amorphous silicon oxide film layer and coming from the surface of the metallic pigment (base material) and, therefore, a color metallic pigment having an interference color with high chroma can be obtained. Further, since the metal particles are directly formed on the surface of the metal oxide layer, the adhesion between the metal oxide layer and the metal particles becomes good and it becomes possible to certainly obtain a color metallic pigment that can have a wide variety of colors and changeful interference colors.

Preferred examples of the metal particles to be used in the present invention include particles each containing at least one component selected from the group consisting of Al (aluminum), Ti (titanium), Cr (chromium), Fe (iron), Co (cobalt), Ni (nickel), Cu (copper), Zn (zinc), Ru (ruthenium), Rh (rhodium), Pd (palladium), Ag (silver), Sn (tin), Pt (platinum), Au (gold) and alloys thereof. When each of the metal particles contains at least one component selected from the metals and the metal alloys, a color metallic pigment that develops an interference color having high chroma can be obtained. Particularly preferred examples of the metal particles include particles each containing at least one element selected from the group consisting of Cu, Ni, and Ag.

The metal particles preferably have an average particle diameter of less than or equal to 50 nm. In this case, the surface of the color metallic pigment having both a region on which the metal particles are not formed and a region on which the metal particles are formed is relatively smooth and, therefore, it becomes possible to obtain a color metallic pigment that can provide a metallic film having an excellent finish appearance. The average particle diameter of the metal particles is more preferably less than or equal to 30 nm. The lower limit of the average particle diameter of the metal particles is not particularly limited, and is preferably greater than or equal to 1 nm. If the average particle diameter is less than 1 nm, light can pass through the metal particles, reflected light coming from the layer of the metal particles is reduced, and the coloring effect by the light interference is weakened, sometimes leading to the decrease in chroma of the resultant color metallic pigment.

In the color metallic pigment according to the present invention, it is particularly preferred that the amorphous silicon oxide film layer has a thickness ranging from 10 to 500 nm and the metal particles have an average particle diameter of less than or equal to 50 nm. In this case, an interference color having particularly high chroma can be developed.

The metal particles formed in the color metallic pigment according to the present invention are so formed as to cover a part of the metal oxide layer, rather than entirely cover the surface of the metal oxide layer. It is preferred that the spacing between the metal particles is less than or equal to 10 nm, because a color metallic pigment having higher chroma can be obtained. In this case, a spacing between the metal particles, which is defined as having a size of less than or equal to 10 nm, corresponds to the region that is not covered with the metal particles. In this case, the lower limit of the spacing is preferably greater than or equal to 0.1 nm.

In the present invention, the metal particles may be deposited in such a manner that two or more particles of the metal particles are overlaid on the metal oxide layer. However, it is preferred that the metal particles are deposited in the form of a single layer of which the depth corresponds to the diameter of a single particle. In this case, an interference color having high chroma can be imparted as the result of the interference between reflected light coming from the metal particles and reflected light reflected on the metallic pigment (i.e., base material) and passing through spaces between the metal particles. Further, it is also preferred that the metal particles are deposited on the metal oxide layer in such a state that the metal particles are not in contact with each other. Most typically, the metal particles are deposited on the metal oxide layer in the form of a single layer in such a state that the metal particles are not in contact with each other and the spacing between the metal particles is less than or equal to 10 nm.

The state of deposition of the metal particles, the average particle diameter of the metal particles and the spacing between the metal particles can be assessed by, for example, the observation of a cross section using a transmission electron microscope (TEM). In this case, for the preparation of a sample for the observation, a method of subjecting the cross section of the color metallic pigment having the metal particles formed thereon to FIB (focused ion beam) processing is preferably employed. This method can determine a part to be processed while viewing an image of scanning ion microscopy (SIM: scanning ion microscopic), and therefore can process a specified part in the sample. The color metallic pigment is processed by the above-mentioned method and the cross section of the metal particles is observed on a transmission electron microscope (TEM) at a 300,000 to 3,000,000-fold magnification.

The method for forming the metal particles is not particularly limited, and a vacuum deposition method, a sputtering method, an electroless plating method or the like can be suitably employed. Among these methods, an electroless plating method is particularly preferred, because this method can deposit the metal particles uniformly with a predetermined spacing as mentioned above and therefore enables the achievement of good chroma.

<Weather-Resistant Covering Film Layer or the Like>

In the present invention, a weather-resistant covering film layer as mentioned below may be formed on the metal particles.

(1) Weather-Resistant Covering Film Layer Including a Film Containing an Oxide, a Hydroxide or a Hydrate Alone or a Film Containing a Mixture Containing the Oxide, the Hydroxide or the Hydrate It is preferred that a weather-resistant covering film layer that includes a film containing at least one of an oxide, a hydroxide and a hydrate alone or a film containing a mixture containing the oxide, the hydroxide or the hydrate is additionally formed. When the weather-resistant covering film layer is formed, a discoloration-preventing effect can be imparted to a coating film containing the color metallic pigment according to the present invention and the weather resistance of the coating film can be improved. Particularly when a metal that easily causes an oxidation reaction or a sulfurization reaction, such as silver and copper, is used for the metal particles, the formation of the weather-resistant covering film layer is effective, because weather resistance can be imparted to the resultant color metallic pigment. In particular, a layer that contains an oxide, a hydroxide or a hydrate each containing at least one element selected from aluminum, silicon and cerium is preferred.

(2) Coupling Agent

For the formation of the metal particles or the above-mentioned weather-resistant covering film layer, it is preferred that the weather-resistant covering film layer is further treated with a coupling agent, particularly a coupling agent containing silicon and/or titanium. In this case, when a coating film is formed from a coating composition containing the color metallic pigment according to the present invention, a coating resin and so on, an effect of improving the adhesiveness of the coating film can be achieved as the result of the improvement in the affinity between the color metallic pigment and the coating resin and so on. A preferred example of the coupling agent is a silane coupling agent. Preferred examples of the silane coupling agent include $R_A$—$Si(OR_B)_3$ and $R_A$—$SiR_B(OR_B)_2$ ($R_A$: alkyl, aryl or alkenyl group having 2 to 18 carbon atoms, $R_B$: alkyl group having 1 to 3 carbon atoms). In these formulae, $R_A$ preferably has a functional group. Examples of the functional group include an amino group, an ureido group, an epoxy group, a sulfide group, a vinyl group, a methacryloxy (methacryl) group, an acryloxy (acryl) group, a mercapto group and a ketimino group.

Preferred specific examples of the silane coupling agent include methyltriethoxysilane, methyltrimethoxysilane, tetraethoxysilane, tetramethoxysilane, tetraisopropoxysilane, 3-aminopropyl-trimethoxysilane, n-methyl-3-aminopropyl-trimethoxysilane, 3-aminopropyl-triethoxysilane, 3-aminopropyl-tris(2-methoxy-epoxy-silane), n-aminoethyl-3-aminopropyltrimethoxysilane, 3-methacryloxypropyl-trimethoxysilane, 3-acryloxypropyl-trimethoxysilane, 3-glycidyloxypropyl-trimethoxysilane, 3-mercaptopropyl-trimethoxysilane, 3-mercaptopropyl-triethoxysilane, 3-mercaptopropyl-methyldimethoxysilane, vinyltrichlorosilane, vinyltrimethoxysilane, vinyltriethoxysilane, vinyl-tris(2-methoxyethoxy)silane, and condensation products thereof.

A titanium coupling agent can also be used preferably as the coupling agent in the present invention, although the types of the titanium coupling agent are fewer than those of the silane coupling agent. In general, the titanium coupling agent has a hydrolyzable group as a hydrophilic group and a side-chain organic functional group as a hydrophobic group. Typically, examples of the hydrolyzable group as a hydrophilic group include an alkoxyl group, and examples of the side-chain hydrolyzable group as a hydrophilic group include a phosphoric acid alkyl ester group, an amino group and a sulfide group. A preferred example of a commercially available product of the titanium coupling agent includes Plenact KR46B produced by Ajinomoto Fine-Techno Co., Inc. For example, Plenact KR46B has such a structure that a group $C_8H_{17}O$— and a group HO—P—$(OC_{13}H_{27})_2$, $C_8H_{17}O$— are coordinated with Ti as the hydrolyzable group and the side-chain organic functional group, respectively.

<Resin Covering Layer>

In the color metallic pigment according to the present invention, a resin covering layer may be formed as an outermost layer. In this case, properties, such as chemical resistance, weather resistance, water resistance and moisture resistance, of a coating film that contains the color metallic pigment can be improved, because the adhesion between the color metallic pigment according to the present invention and a coating resin can be improved upon the formation of a coating film using a coating composition containing the color metallic pigment and the coating resin, resulting in the improvement in physical properties of the coating film.

The monomer component constituting the resin covering layer is not particularly limited, and an example is a copolymer synthesized from at least two monomers including, for example, a reactive monomer having a carboxyl group and/or a phosphoric acid group and a polyfunctional acrylic acid ester monomer having three or more functionalities and/or a polymerizable monomer having a benzene core.

Examples of the reactive monomer having a carboxyl group and/or a phosphoric acid group include acrylic acid, methacrylic acid, maleic acid, crotonic acid, itaconic acid, fumaric acid, 2-methacryloyloxyethyl acid phosphate, di-2-methacryloyloxyethyl acid phosphate, tri-2-methacryloyloxyethyl acid phosphate, 2-acryloyloxyethyl acid phosphate, di-2-acryloyloxyethyl acid phosphate, tri-2-acryloyloxyethyl acid phosphate, diphenyl-2-methacryloyloxyethyl acid phosphate, diphenyl-2-acryloyloxyethyl acid phosphate, dibutyl-2-methacryloyloxyethyl acid phosphate, dibutyl-2-acryloyloxyethyl acid phosphate, dioctyl-2-methacryloyloxyethyl acid phosphate, dioctyl-2-acryloyloxyethyl acid phosphate, 2-methacryloyloxypropyl acid phosphate, bis(2-chloroethyl)vinyl phosphonate and diallyldibutyl phosphonosuccinate.

Examples of the polyfunctional acrylic acid ester monomer having three or more functionalities include trimethylolpropane triacrylate, trimethylolpropane trimethacrylate, tetramethylolpropane triacrylate, tetramethylolpropane tetraacrylate, tetramethylolpropane trimethacrylate, tetramethylolpropane tetramethacrylate, pentaerythritol triacrylate, pentaerythritol tetraacrylate, dipentaerythritol hexaacrylate and ditrimethylolpropane tetraacrylate.

The polyfunctional acrylic acid ester monomer is involved in the three-dimensional crosslinking of a resin, and has an effect of insolubilizing the resin covering layer against an organic solvent and water.

Examples of the polymerizable monomer having a benzene core include styrene, α-methylstyrene, vinyltoluene, divinylbenzene, phenyl vinyl ketone, phenyl vinyl ether, divinylbenzene monoxide phenoxyethyl acrylate, phenoxypolyethylene glycol acrylate and 2-hydroxy-3-phenoxypropyl acrylate.

The copolymerization may be carried out using a monomer as mentioned below besides the above-mentioned monomers. When the below-mentioned monomer is used in the copolymerization, properties such as moisture resistance, weather resistance and adhesiveness of a coating film produced using the color metallic pigment according to the present invention can be further improved.

Methyl (meth)acrylate, ethyl (meth)acrylate, n-butyl (meth)acrylate, isobutyl (meth)acrylate, 2-ethylhexyl (meth) acrylate, isodecyl (meth)acrylate, lauryl (meth)acrylate, stearyl (meth)acrylate, butoxy(meth)acrylate, dimethylaminoethyl (meth)acrylate, diethylaminoethyl (meth)acrylate, 2-hydroxybutyl (meth)acrylate, hydroxyethyl (meth)acrylate, 2-hydroxypropyl (meth)acrylate, methoxyethyl (meth) acrylate, butoxyethyl (meth)acrylate, glycidyl (meth)acrylate, cyclohexyl (meth)acrylate, dicyclopentanyloxyethyl (meth)acrylate, dicyclopentanyl (meth)acrylate, tricyclodecane dimethanol di(meth)acrylate, dicyclopentenyloxyethyl (meth)acrylate, dicyclopentenyloxypropyl (meth)acrylate, dicyclopentenyl (meth)acrylate, isobornyl (meth)acrylate, 1-adamantyl (meth)acrylate, 2-methyl-2-adamantyl (meth) acrylate, 1,3-adamantane dimethanol di(meth)acrylate, and esters of other unsaturated carboxylic acids (e.g., acrylic acid, methacrylic acid, crotonic acid, itaconic acid, citraconic acid).

The main constitution of the color metallic pigment according to the present invention is described above. In the color metallic pigment, it is only necessary that the metal oxide layer and the metal particles are formed in direct contact with one another, and a layer, a granulated material or the like other than the above-mentioned components may be additionally formed as long as the effect of the present invention cannot be deteriorated.

<Coating Composition>

The present invention also relates to a coating composition such as a coating material and an ink, which contains at least the above-mentioned color metallic pigment or a color metallic pigment produced by the below-mentioned production method. The coating composition in the present invention includes, for example, a coating material, a coating film produced using the coating material, an ink and a printed matter produced using the ink. The coating material and the ink may be of an organic-solvent-based type or a water-based type. In a water-based coating material or a water-based ink, the improvement in light resistance and weather resistance is the critical issue. Therefore, the color metallic pigment according to the present invention can be effectively compounded to a water-based coating material or a water-based ink particularly.

The amount of the color metallic pigment to be compounded in the coating composition preferably falls within the range from 0.1 to 30 mass % relative to the amount of the coating composition. When the amount to be compounded is greater than or equal to 0.1 mass %, decorative effects including a metallic effect are good. When the amount is less than or equal to 30 mass %, the weather resistance, corrosion resistance, mechanical strength and so on of the coating composition are good. The amount of the color metallic pigment to be compounded in the coating composition more preferably falls within the range from 1 to 20 mass % relative to the amount of the coating composition.

The coating composition can be obtained, for example, by compounding a coating resin with the color metallic pigment according to the present invention properly. Examples of the coating resin include an acrylic resin, an alkyd resin, a polyester resin, a polyurethane resin, a poly(vinyl acetate) resin, a nitrocellulose resin and a fluororesin.

In the coating composition of the present invention, a color pigment, an extender pigment, a dye or the like other than the color metallic pigment may be used in combination, in addition to the color metallic pigment and the coating resin. Examples of the color metallic pigment to be used in combination include phthalocyanine, quinacridone, isoindolinone, perylene, azo lake, iron oxide, chrome yellow, carbon black, titanium oxide and pearl mica.

In the coating composition of the present invention, in addition to the above-mentioned components, an additive such as water, an organic solvent, a surfactant, a curing agent, an ultraviolet ray absorber, a static electricity elimination agent and a thickening agent may be used, if necessary.

When a coating film is formed using the coating composition of the present invention, the coating film may be formed on an under coating layer or a middle coating layer which is formed by means of electrodeposition coating or the like, and a top-coat layer may be additionally formed on the coating film produced using the coating composition of the present invention.

<Cosmetic>

The present invention also relates to a cosmetic containing at least the above-mentioned color metallic pigment or a color metallic pigment produced by the below-mentioned method.

Heretofore, a pearl pigment and an aluminum pigment have been used for imparting a glossy feeling or brightness to a cosmetic. However, a pearl pigment and an aluminum pigment have the following problems: a pearl pigment has a poor obliterating performance; and an aluminum pigment has a gray color and therefore cannot develop a clear color when mixed with a color pigment. An aluminum pigment has an additional problem that the aluminum pigment easily reacts with water and therefore cannot be used in a water-containing cosmetic.

By compounding the color metallic pigment according to the present invention, it becomes possible to obtain a cosmetic having excellent obliterating power and having a clear color. The color metallic pigment according to the present invention has such a property that the color metallic pigment cannot react when used in a water-containing cosmetic (i.e., stability). Further, the color metallic pigment according to the present invention contains no metal layer unlike a conventional one, and therefore the use applications of the color metallic pigment for cosmetic purposes are not restricted.

The cosmetic having the color metallic pigment according to the present invention compounded is not particularly limited, and examples of specific embodiments of the cosmetic are as follows.

<Embodiments of Cosmetic>

(1) The Types of the Cosmetic Include the Following Items.

Make-up cosmetic (e.g., lipstick, foundation, blush, eye shadow, and nail enamel), hair cosmetic (hair gel, hair wax, hair treatment, shampoo, and hair manicure gel), and basic skin care cosmetic (foundation cream).

(2) Examples of the Constituent Components for the Cosmetic Other than the Color Metallic Pigment According to the Present Invention Include the Following Components.

<Oily Component>

Oils and fats (e.g., olive oil and castor oil), wax (e.g., beeswax, carnauba wax, and lanolin), hydrocarbon oil (e.g., liquid paraffin, squalane, and polybutene), fatty acid ester (e.g., isopropyl myristate, cetyl 2-ethylhexanoate, diisopropyl adipate, and glyceryl trimyristate), higher fatty acid (e.g., oleic acid and isostearic acid), higher alcohol (e.g., isostearyl alcohol and oleyl alcohol), silicone oil (e.g., dimethylpolysiloxane, methylphenylpolysiloxane, and octamethylcyclotetrasiloxane), and fluorine compound (e.g., perfluoro polyether).

<Other Components>

Surfactant, moisturizing agent, polyhydric alcohol, water-soluble polymer, film-forming agent, water-insoluble polymer, polymer emulsion, powder, pigment, dye, lake, lower alcohol, ultraviolet ray absorber, vitamin, antioxidant agent, antibacterial agent, flavoring agent, and water.

<Amount to be Compounded>

In the cosmetic, the color metallic pigment is compounded in an amount of 0.1 to 99 mass %, preferably 1 to 80 mass %.

(3) Preparation Method

Any conventional method for producing a cosmetic can be employed without particular limitation.

As for the method for dispersion, a method using a disper, a method using a roll mill or the like can be employed preferably.

<Method for Producing Color Metallic Pigment>

The color metallic pigment according to the present invention can be produced by, for example, through the following production steps. That is, the color metallic pigment can be produced by a production method including at least: a step of hydrolyzing an organosilicon compound in a solvent mainly containing a hydrophilic solvent and having a metallic pigment dispersed therein to allow amorphous silicon oxide to be deposited on the metallic pigment, thereby forming an amorphous silicon oxide film layer on the surface of the metallic pigment (amorphous silicon oxide film layer formation step); a step of allowing a metal oxide layer containing a metal oxide other than silicon oxide to be deposited on the surface of the amorphous silicon oxide film layer, thereby forming the metal oxide layer (metal oxide layer formation step); and a step of forming metal particles on the surface of the metal oxide layer by an electroless plating method (metal particle formation step).

In the present invention, when an under layer is formed between the metallic pigment and the amorphous silicon oxide film layer, the under layer is firstly formed on the surface of the metallic pigment. Typically, a method is employed, in which the metallic pigment and a solution containing a molybdenum compound and/or a phosphorous compound are stirred or kneaded in the state of a slurry or a paste to form a hydration film containing at least one element selected from molybdenum and phosphorous on the metallic pigment and the resultant product is then heated to convert the hydration film into an under layer.

An amorphous silicon oxide film layer is formed on the under layer (amorphous silicon oxide film layer formation step). An organosilicon compound is hydrolyzed in a solvent in which the metallic pigment having the under layer formed thereon is dispersed and which is mainly containing a hydrophilic solvent to allow the amorphous silicon oxide to be deposited on the metallic pigment (under layer), thereby forming an amorphous silicon oxide film layer on the surface of the metallic pigment (under layer). As for the hydrophilic solvent, methyl alcohol, ethyl alcohol, isopropyl alcohol, n-propyl alcohol, t-butyl alcohol, n-butyl alcohol, isobutyl alcohol, ethyl cellosolve, butyl cellosolve, propylene glycol monobutyl ether, dipropylene glycol monomethyl ether, propylene glycol monopropyl ether, acetone or the like can be used. As for the organosilicon compound, methyltriethoxysilane, methyltrimethoxysilane, tetraethoxysilane, tetramethoxysilane, tetraisopropoxysilane, a condensation product of any one of the above-mentioned compounds, γ-aminopropyltriethoxysilane, N-2-aminoethyl-3-aminopropyltriethoxysilane, N-2-aminoethyl-3-aminopropylmethyldimethoxysilane or the like can be used.

When an alcohol is used as the hydrophilic solvent, the amorphous silicon oxide film layer is formed by forming an alkoxy silicate on the surface of the metallic pigment (under layer), hydrolyzing the alkoxy silicate, and then performing the dehydrative condensation of the resultant product. As for the catalyst for the above-mentioned hydrolysis reaction, an acid or a base can be preferably used.

Subsequently, a metal oxide layer is formed on the surface of the metallic pigment that is covered with the amorphous silicon oxide film layer by the above-mentioned method (metal oxide layer formation step). The metal oxide layer formation step can be carried out as a preceding step of a metal particle formation step as mentioned below. That is, a metal oxide layer is formed on the surface of the metallic pigment having the amorphous silicon oxide film layer formed thereon by a method in which an alkoxide of, for example, at least one metal selected from the group consisting of Mg, Sn, Zn, Co, Ni, Fe, Zr, Ti, and Ce as a metal species capable of forming an active site for depositing the metal particles in the subsequent metal particle formation step is hydrolyzed and deposited by a sol-gel method, a method in which an alkali is added to a metal salt solution containing the above-mentioned metal to neutralize the solution and deposit the metal oxide layer, a method in which the metal pigment is brought into contact with an organic metal compound solution containing the above-mentioned metal, or the like. The detail about this step is as mentioned in the section describing about the metal oxide layer. The metal oxide layer formed in this manner preferably contains an oxide of at least one element selected from the group consisting of Mg, Sn, Zn, Co, Ni, Fe, Zr, Ti, and Ce.

Subsequently, the metal particles are formed in the form of uniform nano-particulate material on the surface of the metal oxide layer by an electroless plating method or the like (metal particle formation step). The electroless plating can be carried out by, for example, a method in which the metallic pigment having the metal oxide layer formed thereon is transformed into a slurry using water as a dispersion medium and then an electroless plating solution is added to the slurry to cause the reaction. Typically, the electroless plating solution contains at least a metal source from which the metal particles are mainly formed, a reducing agent and a complexing agent.

As for the metal source, a water-soluble metal salt containing any one of Al, Ti, Cr, Fe, Co, Ni, Cu, Zn, Ru, Rh, Pd, Ag, Sn, Pt or Au can be used. As for the water-soluble salt, a nitric acid salt, a nitrous acid salt, a sulfuric acid salt, an oxalic acid salt, a carbonic acid salt, a chloride, an acetic acid salt, a lactic acid salt, a sulfamic acid salt, a fluoride, an iodide, a cyanide or the like can be used.

As for the reducing agent, hypophosphorous acid, formaldehyde, boron hydride, dimethylamine borane, trimethylamine borane, hydrazine, glucose, tartaric acid, an alkali metal salt of any one of these compounds, or the like can be used.

As for the complexing agent, a carboxylic acid such as succinic acid, an oxycarboxylic acid such as citric acid and tartaric acid, an organic acid such as glycine, EDTA and aminoacetic acid, an alkali metal salt or an ammonium salt of any one of these acids, or the like can be used. When the complexing agent is used, the metal particles can be formed in a stable manner.

By employing the above-mentioned method, it becomes possible to allow the metal particles to be uniformly deposited on the metal oxide layer with a predetermined spacing as mentioned above (i.e., the formation of the metal particles so as to directly cover a part of the metal oxide layer).

Prior to the metal particle formation step, the metal oxide layer may be subjected to a surface activating treatment with a solution containing Sn, Pt, Pd, Au or the like as a pre-treatment.

In the present invention, it is preferred that an anti-corrosion layer including a film of at least one of an organic compound alone or a surfactant alone or a film of a mixture containing the organic compound or the surfactant is formed on the metal particles. When the anti-corrosion layer contains aluminum and/or silicon, the anti-corrosion layer can be formed by adding a compound containing aluminum and/or silicon to a slurry-like or past-like suspension that is prepared by suspending the metallic pigment having at least the amorphous silicon oxide film layer and the metal particles formed thereon in a hydrophilic solvent and then stirring or kneading the resultant mixture, thereby adhering the compound containing aluminum and/or silicon onto the surface of the metallic pigment.

In the present invention, it is preferred that a step of forming a weather-resistant covering film layer (weather-resistant covering film layer formation step) is included subsequent to the metal particle formation step. When the weather-resistant coating film layer contains aluminum and/or silicon, the metallic pigment having at least the metal particles formed thereon as mentioned above and a solution containing aluminum and/or silicon are stirred or kneaded while keeping the state of a slurry or a paste to form a hydration film and the hydration film is then heated, thereby forming a weather-resistant covering film layer including a film of at least one of an oxide, a hydroxide and a hydrate of aluminum and/or silicon alone or a film of a mixture containing the oxide, the hydroxide or the hydrate. When the weather-resistant covering film layer contains cerium, the metallic pigment having at least the metal particles formed thereon are added to a solution in which cerium acetate, cerium nitrate, a cerium alkoxide, a cerium sol or the like is dissolved or dispersed and the resultant mixture is then stirred or kneaded while being heated and while keeping a basic atmosphere, thereby forming a weather-resistant covering film layer including a film of at least one of an oxide, a hydroxide and a hydrate of cerium alone or a film of a mixture containing the oxide, the hydroxide or the hydrate.

When the above-mentioned weather-resistant covering film layer is formed, it is preferred that a coupling treatment step is employed in combination. For example, when the weather-resistant covering film layer contains aluminum and/or silicon, the coupling treatment is carried out by a method in which the metallic pigment on which the metal particles have been formed and a solution containing aluminum and/or silicon are stirred or kneaded together in a state of a slurry or a paste and then a coupling agent is added to the resultant product, or the like. When the weather-resistant covering film layer contains cerium, the coupling treatment is carried out by a method in which the metallic pigment on which the metal particles have been formed is added to a solution or dispersion of a cerium compound, the resultant mixture is stirred or kneaded while being heated and while keeping a basic atmosphere, and a coupling agent is then added the stirred or kneaded product, or the like. Alternatively, a method in which the metallic pigment on which the weather-resistant covering film layer has been formed is dispersed in a solvent such as isopropyl alcohol to form a slurry and a coupling agent is then added to the slurry, or the like may be employed.

In the present invention, subsequent to the metal particle formation step, a step of forming a resin coating layer as the weather-resistant covering film layer (resin covering layer formation step) may also be included. In the step of forming the resin coating layer, the metallic pigment on which at least the metal particles have been formed is dispersed in a non-polar solvent such as mineral spirit, heptane, octane and isoparafin, the above-mentioned monomer is added to the resultant dispersion, and a polymerization initiator such as benzoyl peroxide, lauroyl peroxide and azobisisobutyronitrile is then added to the resultant mixture under an inert atmosphere at 50 to 150° C., more preferably 70 to 100° C., while mixing by stirring. Subsequently, the stirring is continued until the monomer is fully polymerized (for 1 to 20 hours, more preferably 3 to 10 hours), the resultant slurry is subjected to a solid-liquid separation procedure after the completion of the reaction to produce a past-like composition. In this manner, the resin coating layer can be formed.

The color metallic pigment according to the present invention can be prepared by the above-mentioned method. The color metallic pigment thus prepared may be mixed with a coating resin and, if necessary, other color pigment, other extender pigment, other dye, other additive and so on by a conventional known method, thereby preparing the coating composition according to the present invention. A cosmetic containing the color metallic pigment according to the present invention can be prepared by a conventional known method.

EXAMPLES

The present invention is described below in more detail with reference to specific examples: however, the present invention is not limited to these examples.

Example 1

To 3 g of aqueous hydrogen peroxide containing 30 mass % of hydrogen peroxide was added 0.3 g of a metal molybdenum powder in portions, thereby causing the reaction between these components. The resultant solution was dissolved in 500 g of isopropyl alcohol (hereinafter, abbreviated as "IPA"), and thereto was further added 40 g (i.e., 30 g in terms of aluminum content) of a commercially available aluminum pigment (flaky aluminum, trade name: "5422NS" (produced by Toyo Aluminium K. K.), solid content: 75 mass %, average particle diameter: 19 µm, average thickness: 1 µm)) as a metallic pigment. The resultant was stirred and mixed at 75° C. for 1 hour, thereby obtaining a slurry. In this manner, a metallic pigment having molybdenum oxide formed on the surface thereof was obtained as an under layer.

Subsequently, aqueous ammonia and 80 g of water were added to the slurry to adjust the pH value of the slurry to 10.0. To the pH-adjusted slurry (i.e., solvent mainly containing a hydrophilic solvent, in which the metallic pigment having the under layer formed thereon was dispersed) was gradually dropwise added a solution prepared by dissolving 40 g of tetraethoxysilane as an organosilicon compound in 40 g of IPA, and the resultant was further stirred and mixed at 75° C. for 2 hours to hydrolyze the organosilicon compound, thereby allowing amorphous silicon oxide to be deposited on the metallic pigment (under layer). Subsequently, the slurry was subjected to a solid-liquid separation using a filter, thereby forming an amorphous silicon oxide film layer on the surface of the metallic pigment (amorphous silicon oxide film layer formation step). Hereinafter, the metallic pigment in this state was termed "silica-coated aluminum pigment".

Then, 10 g of the silica-coated aluminum pigment obtained in the above-mentioned step was dispersed in 300 g of an aqueous solution containing 40 g of tin chloride and 2 g of hydrochloric acid with stirring, and then a 10% aqueous sodium hydroxide solution was dropwise added thereto in portions until the pH value of the solution reached 7.0 while keeping the slurry temperature at 30° C. After the completion of the dropwise addition, the stirring was continued for 1 hour. The resultant slurry was again subjected to a solid-liquid separation procedure and washed with water to allow a tin oxide layer to be deposited on the surface of the silica-coated aluminum pigment, thereby fainting a tin oxide layer as a metal oxide layer (metal oxide layer formation step). Hereinafter, the metallic pigment in this state was termed "metal-oxide-layer-covered aluminum pigment".

Subsequently, 10 g of the metal-oxide-layer-covered aluminum pigment obtained in the above-mentioned step was dispersed in 800 g of an electroless silver plating solution containing 3 g of silver nitrate, 2 g of formaldehyde and 10 g of aqueous ammonia, and the resultant was held at 30° C. for 1 hour. In this manner, metal particles (silver particles) were formed on the surface of the metal oxide layer by an electroless plating method (metal particle formation step). Hereinafter, the metallic pigment in this state was termed "metal-particles-adhered aluminum pigment". The metal-particles-adhered aluminum pigment had such a form that the metal particles were uniformly formed with a regular spacing on the metal oxide layer (i.e., the metal particles were so formed as to directly cover a part of the metal oxide layer).

The thus-obtained metal-particles-adhered aluminum pigment was subjected to a solid-liquid separation procedure and then dried, thereby obtaining a color aluminum pigment having a blue color that was a color aluminum pigment according to the present invention. The color aluminum pigment was visually observed, and it was found that the color aluminum pigment had an interference color that turned from a bluish-purple color to a dark brown color when viewed from different angles and had a good metallic feeling. The color aluminum pigment was also observed on a transmission electron microscope, and it was found that the amorphous silicon oxide film layer had a thickness of 70 nm, the metal oxide layer had a thickness of 2 nm, and the metal particles had an average particle diameter of 5 nm and were uniformly formed with a spacing of 0.5 nm on the metal oxide layer.

Example 2

A silica-coated aluminum pigment (10 g) obtained in the same amorphous silicon oxide film layer formation step as in Example 1 was dispersed in 500 g of an aqueous solution containing 50 g of cerium nitrate with stirring, and thereto was dropwise added a 5% aqueous ammonia solution in portions until the pH value of the solution reached 7.0 while keeping the slurry temperature at 40° C. After the completion of the dropwise addition, the stirring was continued for 1 hour. The resultant slurry was again subjected to a solid-liquid separation procedure and washed with water to allow a cerium oxide layer to be deposited on the surface of the silica-coated aluminum pigment, thereby forming the cerium oxide layer as a metal oxide layer (metal oxide layer formation step). Hereinafter, the metallic pigment in this state was termed "metal-oxide-layer-covered aluminum pigment", as in the case of Example 1.

Then, the resultant slurry was subjected to a solid-liquid separation procedure, washed with water, then dispersed in 900 g of an electroless silver plating solution containing 3 g of silver nitrate, 40 g of glucose and 20 g of aqueous ammonia, and held at 40° C. for 10 minutes. In this manner, metal particles (silver particles) were formed on the surface of the metal oxide layer by an electroless plating method (metal particle formation step). The metallic pigment in this state was termed "metal-particles-adhered aluminum pigment", as in the case of Example 1. The metal-particles-adhered aluminum pigment had such a form that the metal particles were uniformly formed with a regular spacing on the metal oxide layer (i.e., the metal particles were so formed as to directly cover a part of the metal oxide layer).

The thus-obtained metal-particles-adhered aluminum pigment was subjected to a solid-liquid separation procedure and dried, thereby obtaining a color aluminum pigment having an orange color that was a color aluminum pigment according to the present invention. The color aluminum pigment was visually observed, and it was found that the color aluminum pigment had an interference color that turned from a green color to an orange color when viewed from different angles and had a good metallic feeling. The color aluminum pigment was also observed on a transmission electron microscope, and it was found that the amorphous silicon oxide film layer had a thickness of 70 nm, the metal oxide layer had a thickness of 5 nm, and the metal particles had an average particle diameter of 7 nm and were formed uniformly with a spacing of 0.8 nm on the metal oxide layer.

Example 3

A silica-coated aluminum pigment (10 g) obtained in the same amorphous silicon oxide film layer formation step as in Example 1 was dispersed in 400 g of an aqueous solution containing 30 g of tetrabutoxytitanium with stirring, and thereto was dropwise added a 5% aqueous ammonia solution in portions until the pH value of the solution reached 10.0. After the completion of the dropwise addition, the stirring was continued for 1 hour. The resultant slurry was subjected to a solid-liquid separation procedure and washed with water to allow a titanium oxide layer to be deposited on the surface of the silica-coated aluminum pigment, thereby forming a titanium oxide layer as a metal oxide layer (metal oxide layer formation step). Hereinafter, the metallic pigment in this state was termed "metal-oxide-layer-covered aluminum pigment", as in the case of Example 1.

Then, the resultant slurry was subjected to a solid-liquid separation procedure, washed with water, then dispersed in 200 g of an electroless silver plating solution containing 3 g of silver nitrate, 15 g of potassium sodium tartrate and 15 g of aqueous ammonia, and held at 35° C. for 40 minutes. In this manner, metal particles (silver particles) were formed on the surface of the metal oxide layer by an electroless plating method (metal particle formation step). The metallic pigment in this state was termed "metal-particles-adhered aluminum pigment", as in the case of Example 1. The metal-particles-adhered aluminum pigment had such a form that the metal particles were uniformly formed with a regular spacing on the metal oxide layer (i.e., the metal particles were so formed as to directly cover a part of the metal oxide layer).

The thus-obtained metal-particles-adhered aluminum pigment was subjected to a solid-liquid separation procedure and dried, thereby obtaining a color aluminum pigment having a green color that was a color aluminum pigment according to the present invention. The color aluminum pigment was visually observed, and it was found that the color aluminum pigment had an interference color that turned from a blue color to a green color when viewed from different angles and had a good metallic feeling. The color aluminum pigment was also observed on a transmission electron microscope, and it was found that the amorphous silicon oxide film layer had a thickness of 70 nm, the metal oxide layer had a thickness of 10 nm, and the metal particles had an average particle diameter of 12 nm and were formed uniformly with a spacing of 1 nm on the metal oxide layer.

Example 4

A silica-coated aluminum pigment (10 g) obtained in the same amorphous silicon oxide film layer formation step as in Example 1 was dispersed in 300 g of an aqueous solution containing 50 g of zinc chloride with stirring, and thereto was then dropwise added a 5% aqueous ammonia solution in portions until the pH value of the solution reached 7.0. After the completion of the dropwise addition, the stirring was continued for 1 hour. The resultant slurry was again subjected to a solid-liquid separation procedure and washed with water to allow a zinc oxide layer to be deposited on the surface of the silica-coated aluminum pigment, thereby forming the zinc oxide layer as a metal oxide layer (metal oxide formation step). Hereinafter, the metallic pigment in this state was termed "metal-oxide-layer-covered aluminum pigment", as in the case of Example 1.

Then, the resultant slurry was subjected to a solid-liquid separation procedure, washed with water, then dispersed in 900 g of an electroless silver plating solution containing 3 g of silver nitrate, 40 g of glucose and 20 g of aqueous ammonia, and then held at 40° C. for 10 minutes. In this manner, metal particles (silver particles) were formed on the surface of the metal oxide layer by an electroless plating method (metal particle formation step). The metallic pigment in this state was termed "metal-particles-adhered aluminum pigment", as in the case of Example 1. The metal-particles-adhered aluminum pigment had such a form that the metal particles were uniformly formed with a regular spacing on the metal oxide layer (i.e., the metal particles were so formed as to directly cover a part of the metal oxide layer).

The thus-obtained metal-particles-adhered aluminum pigment was subjected to a solid-liquid separation procedure and dried, thereby obtaining a color aluminum pigment having an orange color that was a color aluminum pigment according to the present invention. The color aluminum pigment was visually observed, and it was found that the color aluminum pigment had an interference color that turned from an orange color to a blue color when viewed from different angles and had a good metallic feeling. The color aluminum pigment was also observed on a transmission electron microscope, and it was found that the amorphous silicon oxide film layer had a thickness of 70 nm, the metal oxide layer had a thickness of 5 nm, and the metal particles had an average particle diameter of 20 nm and were formed uniformly with a spacing of 1 nm on the metal oxide layer.

Example 5

To a slurry prepared by dispersing 30 g of the color metallic pigment obtained in Example 1 in 200 g of IPA were added 5 g of tetraethoxysilane and 15 g of a 10 mass % aqueous urea solution. The resultant was stirred and mixed at 75° C. for 5 hours to bring the components to react with one another, thereby forming a weather-resistant covering film layer containing silicon oxide on the surface of the metallic pigment (weather-resistant covering film layer formation step). The slurry was filtrated, thereby obtaining a color metallic pigment in which the weather-resistant covering film layer having a solid content of 60 mass % was formed on the outermost surface thereof. Hereinafter, the metallic pigment in this state was termed "weather-resistant-covering-film-layer-coated aluminum pigment".

Then, to a slurry prepared by dispersing 30 g of the weather-resistant-covering-film layer-coated aluminum pigment obtained in the above-mentioned step in 400 g of IPA was added 2 g of γ-aminopropyltriethoxysilane. The resultant was stirred and mixed at 75° C. for 1 hour to bring these components to react with one another, thereby further coupling-treating the surface of the weather-resistant covering film layer (coupling treatment step). The slurry was filtrated, thereby obtaining a color aluminum pigment having a solid content of 60 mass % as a color metallic pigment according to the present invention. The resultant color aluminum pigment had the same color phase as that of the product of Example 1. The color aluminum pigment was also observed on a transmission electron microscope, and it was found that the weather-resistant covering film layer had a thickness of 20 nm.

Example 6

The same procedure as in Example 1 was carried out, except that a silver-coated flaky glass (thickness: 1 μm, average particle diameter: 25 μm, amount of silver covered: 30 mass %) was used as the metallic pigment, thereby obtaining a color metallic pigment. The resultant color metallic pigment had an interference color that turned from an orange color to a yellow color when viewed from different angles. The color metallic pigment was also observed on a transmission electron microscope, and it was found that the amorphous silicon oxide film layer had a thickness of 90 nm, the metal oxide layer had a thickness of 4 nm, and the metal particles had an average particle diameter of 15 nm and were uniformly formed with a spacing of 0.3 nm on the metal oxide layer.

Comparative Example 1

The same procedure as in Example 1 in a pamphlet of International Publication No. 2007/094253 (PTL 12) was carried out, thereby producing a color metallic pigment.

That is, to 3 g of aqueous hydrogen peroxide containing 30 mass % of hydrogen peroxide was added 0.3 g of a metal molybdenum powder in portions, thereby causing the reaction between these components. The resultant solution was dissolved in 500 g of isopropyl alcohol (hereinafter, abbreviated as "IPA"), and thereto was further added 40 g (i.e., 30 g in terms of aluminum content) of a commercially available aluminum pigment ("5422NS" produced by Toyo Aluminium K. K., a solid content: 75 mass %, average particle diameter: 19 μm, average thickness: 1 μm) as a metallic pigment, and stirred and mixed at 75° C. for 1 hour, thereby obtaining a slurry.

Subsequently, to the slurry were added aqueous ammonia and 80 g of water, thereby adjusting the pH value of the slurry to 10.0. To the pH-adjusted slurry was gradually dropwise added a solution prepared by dissolving 40 g of tetraethoxysilane in 40 g of IPA, and the resultant was further stirred and mixed at 75° C. for 2 hours. Subsequently, the slurry was subjected to a solid-liquid separation procedure using a filter to form an amorphous silicon oxide film layer on the surface of the metallic pigment (amorphous silicon oxide film layer formation step), thereby preparing a silica-coated aluminum pigment.

The resultant silica-coated aluminum pigment (10 g) was dispersed in 300 g of an aqueous solution containing 40 g of tin chloride and 2 g of hydrochloric acid at 30° C. for 1 hour, again subjected to a solid-liquid separation procedure, and washed with water, thereby forming a metal layer on the surface of the silica-coated aluminum pigment (metal layer formation step), thereby preparing a metal-layer-covered aluminum pigment.

The resultant metal-layer-covered aluminum pigment was dispersed in 800 g of an electroless silver plating solution containing 3 g of silver nitrate, 2 g of formaldehyde and 10 g of aqueous ammonia and held at 30° C. for 1 hour to form metal particles on the surface of the metal layer (metal particle formation step), thereby obtaining a metal-particles-adhered aluminum pigment. The resultant metal-particles-adhered aluminum pigment was subjected to a solid-liquid separation procedure and dried, thereby obtaining a color metallic pigment having a blue color. The color metallic pigment was visually observed, and it was found that the color aluminum pigment had an interference color that turned from a bluish-purple color to a dark brown color when viewed from different angles and had a good metallic feeling.

The color metallic pigment had such a structure that a metal layer was formed in place of the metal oxide layer in the color metallic pigment of the present invention.

Comparative Example 2

A silica-coated aluminum pigment (10 g) obtained in the same amorphous silicon oxide film layer formation step as in Example 1 was dispersed in 800 g of an electroless silver plating solution containing 3 g of silver nitrate, 2 g of formaldehyde and 10 g of aqueous ammonia and held at 30° C. for 1 hour. The resultant flake was subjected to a solid-liquid separation procedure and dried. As a result, an aluminum pigment having a pale blue color was obtained. The aluminum pigment was visually observed, and it was found that the aluminum pigment had poor color flop properties and low chroma.

The aluminum pigment had such a structure that no metal oxide layer was formed in the color metallic pigment of the present invention.

<Metal Particle Adhesion Strength Test>

To 5 g of each of the color metallic pigments obtained in Example 1 and Comparative Example 1 was added 3 g of mineral spirit. The resultant was placed in a 100-ml PP (polypropylene) cup, and manually kneaded with a spatula 60 times in total for 5 minutes for each time. Before and after the kneading, 1.5 g (in terms of solid content) of each of the color metallic pigments was weighed in a 100-ml PP cup and thereto was added 50 g of an ambient-drying acrylic lacquer ("Auto Clear Super" produced by Nippon Paint Co., Ltd.), and the resultant was dispersed with a disper for 3 minutes, thereby producing a coating material. The resultant coating material was applied on a piece of two-sided art paper with a 225 μm doctor blade, and dried. Thereafter, the coating material was assessed on the degree of discoloration (i.e., adhesion strength of metal particles) before and after the kneading by gray scale assessment in accordance with JIS L0804.

Specifically, it is determined that, the color difference of the color metallic pigment between before and after the kneading becomes smaller and the adhesion strength of the metal particles becomes stronger with the increase in gray scale value in the gray scale assessment. The adhesion strength was assessed by this method. In the color metallic pigment of Example 1, the color difference was small in the gray scale assessment, therefore the adhesion strength was high, and substantially no color loss was observed. In the color metallic pigment obtained in Comparative Example 1, on the contrary, the color difference was large in the gray scale assessment, therefore the adhesion strength was poor, a significant level of color loss was observed, and the color was turned as close to silver.

The same test was carried out on the color metallic pigments obtained in Examples 2 to 6, and substantially no color loss was observed in each of the color metallic pigments. The same test was also carried out on the color metallic pigment of Comparative Example 2, and color loss was observed. With respect to each of the color metallic pigments, the above-mentioned adhesion strength test on the metal particles was carried out by the gray scale assessment in accordance with JIS L0804. The results are shown in Table 1.

That is, in the color metallic pigments of Comparative Examples 1 to 2, the metal particle adhesion forces were weaker than those of the color metallic pigments of Examples 1 to 6, and the metal particles were detached from the metallic pigments, resulting in the decrease in the interference activity and the occurrence of color loss.

<Preparation of Water-Based Coating Material>
(Preparation of Rheology-Controlling Agent)

A polyamide-type rheology-controlling agent ("Disparlon AQ600" (trade name) produced by Kusumoto Chemicals, Ltd.) (19.5 parts by mass), 6 parts by mass of butyl cellosolve and 106.5 parts by mass of ion-exchanged water were stirred and mixed for 1 hour to prepare a rheology-controlling agent (composition 1).

(Preparation of Resin Solution)

An acryl copolymer ("Setaqua 6802" (trade name) produced by Neuplex) (27.9 parts by mass), 16.8 parts by mass of polyurethane dispersion A ("Bayhydrol XP 2621" (trade name) produced by Bayer Material Science), 4.1 parts by mass of polyurethane dispersion B ("Bayhydrol PT241" (trade name) produced by Bayer Material Science), 1.9 parts by mass of a melamine resin solution ("Cymel327" (trade name) produced by Mitsui Cytec Ltd.), 5.3 parts by mass of butyl cellosolve, 0.3 parts by mass of an anti-foaming/leveling agent ("AQ7120" (trade name) produced by Kusumoto Chemicals, Ltd.) and 12.4 parts by mass of ion-exchanged water were mixed, and stirred for 30 minutes or longer to prepare a resin solution (composition 2).

(Preparation of Metallic Base)

A dispersant ("AQ320" (trade name) produced by Kusumoto Chemicals, Ltd.) (0.4 parts by mass) and butyl cellosolve were added to each of the color metallic pigments obtained in the above-mentioned Examples and Comparative Examples in an amount corresponding to 4.4 parts by mass of the volatile content so that the total amount was 15.00 parts by mass, and the resultant was stirred and mixed for 10 minutes. In this manner, a metallic base (composition 3) was prepared.

(Preparation of Water-Based Base Metallic Coating Material)

The metallic base (composition 3) (10.5 parts by mass) was added to 96.2 parts by mass of the resin solution (composition 2), and the resultant was stirred and mixed for 10 minutes or longer. Then, 12.3 parts by mass of the rheology-controlling agent (composition 1) was gradually added to the mixture, and the resultant was further stirred and mixed for 10 minutes. Subsequently, a 10% aqueous dimethylethanolamine solution was added so that the pH value of the mixture reached 8.3±0.1, and the resultant was further stirred and mixed for 10 minutes or longer. Finally, a proper amount of ion-exchanged water was added thereto so that the viscosity was a reference value (as measured on Ford cup No. 4 for 25 seconds), and the resultant was stirred and mixed for 10 minutes or longer. The product thus prepared was used as a water-based base metallic coating material.

(Preparation of Coating Material for Clear Coat)

Polyacrylate ("Desmophen A870BA" (trade name) produced by Bayer Material Science) (51.15 g), 0.53 g of additive A (10% solution of "Baysilone Paint Additive OL17" (trade name) produced by Borchers in xylene), 0.53 g of additive B (1% solution of "Modaflow" (trade name) produced by Monsanto in xylene), 5.3 g of additive C (10% solution of "Tinuvin292" (trade name) produced by Ciba Spezialitatenchemie Lampertheim in xylene), 10.7 g of additive D (10% solution of "Tinuvin1130" (trade name) produced by Ciba Spezialitatenchemie Lampertheim in xylene), 10.17 g of dilution solvent A (1-methoxy propyl acetate:solvent naphtha=1:1 (by mass)), and 2.13 g of dilution solvent B (butyl glycol acetate) were stirred and mixed for 30 minutes or longer. Subsequently, 19.49 g of a solution prepared by diluting isocyanurate ("Sumidur N3300" (trade name) produced by Sumika Bayer Urethane Co., Ltd.) and a mixed solvent (butyl acetate:solvent naphtha=1:1 (by mass)) at a proportion of 9:1 (by mass) was added thereto, and the resultant was stirred and mixed for 30 minutes or longer. The resultant was used as a coating material for a clear coat.

<Method for Producing Coated Plate>

The water-based base metallic coating material prepared above was spray-coated onto a metal plate (made from soft steel). The resultant spray-coated plate was set at ambient temperature for 5 minutes or longer, and the spray-coated plate was then dried at 80° C. for 3 minutes. Thereafter, the spray-coated plate was set at ambient temperature for 10 minutes or longer, and then the spray-coated plate was further coated with the above-mentioned coating material for a clear coat by spraying. After the application of the clear coat, the resultant was set at ambient temperature for 10 minutes or longer, and then baked at 130° C. for 30 minutes. In this manner, a coated plate that was spray-coated was obtained. In the spray coating, the coating conditions were adjusted so that the coating film on the coated plate was as follows: the thickness of the water-based metallic coating film: 14 to 18 μm, and the thickness of the clear coat coating film: 35 to 40 μm.

<Water (Moisture) Resistance Test on Coating Film>

The coated plate obtained by the above-mentioned "method for producing coated plate" was held for 10 days on a moisture-resistance test machine that had been kept at a temperature of 40° C. and a humidity of 98% or more. Thereafter, the color difference of the coating film was assessed.

(Color Difference)

With respect to the coated plate obtained by the above-mentioned "method for producing coated plate", measurement was carried out on values of $L^*_{45}$, $a^*_{45}$ and $b^*_{45}$ of the coating film formed on the coated plate at an observation angle of 45 degrees (wherein light was received in the normal direction of the coating film) using a multi-angle color sensor ("X-Rite MA-68II" (trade name) manufactured by X-Rite Incorporated), and the color difference $\Delta E^*_{45}$ of the coating film before and after the test carried out using the above-mentioned moisture test machine was determined. The rating in the assessment is as follows: "excellent": $\Delta E^*_{45}$ was less than 3, "good": ΔE*45 was greater than or equal to 3 and less than 7, and "poor": $\Delta E^*_{45}$ is greater than or equal to 7. The results are shown in Table 1.

<Weather Resistance Test on Coating Film>

The coated plate obtained by the above-mentioned "method for producing coated plate" was placed in a super-xenon accelerated weather resistance test machine ("SUGA SX75" (trade name) produced by Suga Test Instruments Co., Ltd.), and tested for 1500 hours. Thereafter, the color difference of the coating film was assessed. The conditions for the accelerated weather resistance test with super-xenon are as follows.

Irradiation light amount of xenon lamp: 180 W/m²
Black reference panel temperature: 63° C.
Rain condition: 12 minutes per 1 cycle (180 minutes)
(Color Difference)

With respect to the coated plate obtained by the above-mentioned "method for producing coated plate", measurement was carried out on values of $L^*_{45}$, $a^*_{45}$ and $b^*_{45}$ of the coating film formed on the coated plate at an observation angle of 45 degrees (wherein light was received in the normal direction of the coating film) using a multi-angle color sensor ("X-Rite MA-68II" (trade name) manufactured by X-Rite Incorporated), and the color difference $\Delta E^*_{45}$ of the coating film before and after the test carried out using the super-xenon accelerated weather resistance test machine was determined. The rating in the assessment is as follows: "excellent": $\Delta E^*_{45}$ was less than 3, "good": $\Delta E^*_{45}$ was greater than or equal to 3 and less than 7, and "poor": $\Delta E^*_{45}$ is greater than or equal to 7. The results are shown in Table 1.

TABLE 1

|  | Metal particle adhesion strength test | Water (moisture) resistance test on coating film | Weather resistance test on coating film |
| --- | --- | --- | --- |
| Example 1 | 5 | Excellent | Excellent |
| Example 2 | 5 | Excellent | Excellent |
| Example 3 | 4 | Good | Good |
| Example 4 | 5 | Excellent | Excellent |
| Example 5 | 5 | Excellent | Excellent |
| Example 6 | 5 | Excellent | Excellent |
| Comparative Example 1 | 1 | Poor | Poor |
| Comparative Example 2 | 2 | Poor | Poor |

As apparent from Table 1, the color metallic pigment of each of Examples had superior results in all of the "metal particle adhesion strength test", "water (moisture) resistance test on coating film" and "weather resistance test on coating film" compared with those of the color metallic pigment of each of Comparative Examples. From the above-mentioned results, it was confirmed that the color metallic pigment having the constitution of the present invention can develop a wide variety of colors and changeful interference colors in a stable manner while keeping light resistance, weather resistance and obliterating power at good levels. The "metal particle adhesion strength test" mainly assesses obliterating power, the "weather resistance test on coating film" mainly assesses light resistance and weather resistance, and the "water (moisture) resistance test on coating film" mainly assesses whether or not a wide variety of colors and changeful interference colors can be developed in a stable manner.

<Production of Cosmetic>

Various cosmetics were produced in accordance with the formulations mentioned below using each of the color metallic pigments of Example 1 to 6, and the resultant cosmetics were compared with conventional commercially available cosmetics.

Examples 7 to 12

Eye Shadow (Stick Type)

| (1) Talc | 5.0 parts by mass |
| --- | --- |
| (2) Titanium dioxide | 3.0 parts by mass |
| (3) Color metallic pigment | 50.0 parts by mass |

-continued

| (4) Carnauba wax | 10.0 parts by mass |
| --- | --- |
| (5) Solid paraffin | 5.0 parts by mass |
| (6) Lanolin derivative | 5.0 parts by mass |
| (7) Squalane | 20.9 parts by mass |
| (8) Sorbitan sesquioleate ester | 1.0 part by mass |
| (9) Flavor | 0.1 parts by mass |

Color metallic pigment (3) corresponds to each of the color metallic pigments of Examples 1 to 6. The eye shadow produced using the color metallic pigment of Example 1 corresponds to the eye shadow of Example 7, and the eye shadows produced in the same manner using the color metallic pigments of Examples 2 to 6 correspond to the eye shadows of Examples 8 to 12, respectively. The same applies to Examples 13 to 24 mentioned below.

Examples 13 to 18

Hair Cosmetic (Hair Gel)

| (1) Carboxyvinyl polymer | 5.0 parts by mass |
| --- | --- |
| (2) Ethyl alcohol | 2.0 parts by mass |
| (3) PEG 1500 | 1.0 part by mass |
| (4) Aminomethyl propanol | 1.5 parts by mass |
| (5) Methylparaben | 0.1 parts by mass |
| (6) Color metallic pigment | 7.0 parts by mass |
| (7) Purified water | 83.4 parts by mass |

Examples 19 to 24

Nail Enamel

| (1) Nitrocellulose (½ seconds) | 6.5 parts by mass |
| --- | --- |
| (2) Nitrocellulose (⅛ seconds) | 11.0 parts by mass |
| (3) Toluenesulfonamide resin | 12.5 parts by mass |
| (4) Acetotributyl citrate | 5.3 parts by mass |
| (5) Camphor | 1.0 part by mass |
| (6) n-Butyl alcohol | 0.5 parts by mass |
| (7) Ethyl alcohol | 4.5 parts by mass |
| (8) Ethyl acetate | 15.0 parts by mass |
| (9) Butyl acetate | 30.0 parts by mass |
| (10) Color metallic pigment | 13.7 parts by mass |

In all cases, cosmetics having a superior obliterating performance and gloss and clearer colors compared with conventional cosmetics were obtained.

Embodiments and specific examples of the present invention are described above. However, proper combinations of the constitutions of the respective embodiments and the respective specific examples are also originally intended.

The now disclosed embodiments and specific examples are to be considered in all respects only as illustrative and not restrictive. The scope of the present invention is described by claims rather than the above-mentioned description, and all changes which come within the meaning and range of equivalency of the claims are to be embraced within their scope.

The invention claimed is:

1. A color metallic pigment comprising at least a metallic pigment, an amorphous silicon oxide film layer that is formed on the surface of the metallic pigment, a metal oxide layer that is formed on the surface of the amorphous silicon oxide film layer and comprises a metal oxide other than silicon oxide, and metal particles that are formed on the surface of the metal oxide layer, wherein the amorphous silicon oxide film layer has a thickness of 10 to 500 nm, wherein the metal oxide layer has a thickness of 0.1 to 10 nm and consists of an oxide of one element selected from the group consisting of Mg, Sn, Zn, Co, Ni, Fe, Zr, Ti, and Ce, wherein the metal particles are so formed as to directly cover a part of the metal oxide layer, the surface of the metal oxide layer has a region on which the metal particles are not formed, the region corresponds to the spacing between the metal particles, the spacing is greater than or equal to 0.1 and less than or equal to 10 nm, and the metal particles have an average particle diameter of less than or equal to 50 nm, wherein the strength of the metal particle adhesion as well as the water and weather resistance are enhanced.

2. The color metallic pigment according to claim 1, wherein each of the metal particles comprises at least one element selected from the group consisting of Cu, Ni, and Ag.

3. A method for producing the color metallic pigment as recited in claim 1, comprising at least the steps of:

hydrolyzing an organosilicon compound in a solvent mainly containing a hydrophilic solvent and having a metallic pigment dispersed therein to allow amorphous silicon oxide to be deposited on the metallic pigment, thereby forming an amorphous silicon oxide film layer on the surface of the metallic pigment;

allowing a metal oxide layer comprising a metal oxide other than silicon oxide to be deposited on the surface of the amorphous silicon oxide film layer, thereby forming the metal oxide layer; and forming metal particles on the surface of the metal oxide layer by an electroless plating method.

4. The method for producing the color metallic pigment according to claim 3, wherein the metal oxide layer comprises an oxide of at least one element selected from the group consisting of Mg, Sn, Zn, Co, Ni, Fe, Zr, Ti, and Ce.

5. A coating composition containing at least the color metallic pigment as recited in claim 1.

6. A cosmetic containing at least the color metallic pigment as recited in claim 1.

7. The color metallic pigment of claim 1, wherein an average particle diameter of the metallic pigment is in the range of 2 to 300 μm.

8. The color metallic pigment of claim 7, wherein a ratio of the average particle diameter A to an average thickness B (A/B) of the metallic pigment is within the range of 5 to 1000.

9. A color metallic pigment which consists essentially of:

a metallic pigment, an amorphous silicon oxide film layer disposed on the surface of the metallic pigment, a metal oxide layer, other than silicon oxide, disposed on the surface of the amorphous silicon oxide film layer, and metal particles disposed on the surface of the metal oxide layer, wherein the amorphous silicon oxide film layer has a thickness of 10 to 500 nm, wherein the metal oxide layer has a thickness of 0.1 to 10 nm and consists essentially of an oxide of at least one element selected from the group consisting of Mg, Sn, Zn, Co, Ni, Fe, Zr, Ti and Ce, wherein the metal particles comprise at least one element selected from the group consisting of Cu, Ni and Ag and are disposed to directly cover a part of the metal oxide layer, whereby the surface of the metal oxide layer has a region on which the metal particles are not formed, said region corresponding to a spacing between the metal particles which is greater than or equal to 0.1 nm and less than or equal to 10 nm, and the metal particles have an average particle diameter of 5 to 50 nm, and wherein the strength of the metal particle adhesion as well as the water and weather resistance are enhanced.

10. The color metallic pigment of claim 9, wherein the metallic pigment is selected from the group consisting of Al, Cu, Zn, Ti, Fe, Ni, Cr, and alloys thereof.

11. The color metallic pigment of claim 10, wherein the metallic pigment has an average, longer particle diameter of 2 to 300 μm.

12. The color metallic pigment of claim 11, wherein the metallic pigment has a thickness of 0.01 to 5 μm.

13. The color metallic pigment of claim 9, wherein a ratio of the average particle diameter A to the average thickness B (A/B) is 5 to 1000.

14. The color metallic pigment of claim 1, wherein the metal particles are formed as a single layer.

15. The color metallic pigment of claim 1, wherein the metal particles are not in contact with each other.

* * * * *